United States Patent
Xu

(10) Patent No.: US 9,616,415 B2
(45) Date of Patent: Apr. 11, 2017

(54) STEAM RE-CALCINATION OF MIXED METAL OXIDE CATALYSTS

(75) Inventor: Jinsuo Xu, Fort Washington, PA (US)

(73) Assignee: ROHM AND HAAS COMPANY, Philadelphia, PA (US)

( * ) Notice: Subject to any disclaimer, the term of this patent is extended or adjusted under 35 U.S.C. 154(b) by 26 days.

(21) Appl. No.: 14/007,167

(22) PCT Filed: Mar. 21, 2012

(86) PCT No.: PCT/US2012/029857
§ 371 (c)(1),
(2), (4) Date: Sep. 24, 2013

(87) PCT Pub. No.: WO2012/134898
PCT Pub. Date: Oct. 4, 2012

(65) Prior Publication Data
US 2014/0031585 A1    Jan. 30, 2014

Related U.S. Application Data

(60) Provisional application No. 61/467,418, filed on Mar. 25, 2011.

(51) Int. Cl.
| | | |
|---|---|---|
| *C07C 51/215* | (2006.01) | |
| *B01J 27/057* | (2006.01) | |
| *B01J 23/00* | (2006.01) | |
| *B01J 23/652* | (2006.01) | |
| *B01J 35/00* | (2006.01) | |

(Continued)

(52) U.S. Cl.
CPC ......... *B01J 27/0576* (2013.01); *B01J 23/002* (2013.01); *B01J 23/6525* (2013.01); *B01J 35/002* (2013.01); *B01J 37/0036* (2013.01); *B01J 37/036* (2013.01); *B01J 37/10* (2013.01); *C07C 51/215* (2013.01); *B01J 2523/00* (2013.01)

(58) Field of Classification Search
CPC .. B01J 23/002; B01J 23/6525; B01J 27/0576; B01J 37/0036; B01J 37/036; B01J 37/10; B01J 2523/55; B01J 2523/56; B01J 2523/64; B01J 2523/68; B01J 2523/824; C07C 51/215; C07C 57/04
See application file for complete search history.

(56) References Cited

U.S. PATENT DOCUMENTS 5,380,933 A * 1/1995 Ushikubo et al. ............ 562/549
5,472,925 A * 12/1995 Ushikubo et al. ............ 502/312
(Continued)

FOREIGN PATENT DOCUMENTS

| EP | 1260495 | 8/2004 |
| WO | 2009106474 | 9/2009 |

OTHER PUBLICATIONS

X-ray Diffraction (XRD) and Reflectivity (XRR)., MRL Frederick Seitz Materials Research Laboratory., http://mrl.illinois.edu/facilities/center-microanalysis-materials/cmm-instruments/x-ray-diffraction-xrd-and-reflectivity-xrr. 2014.
(Continued)

*Primary Examiner* — Jun Li
(74) *Attorney, Agent, or Firm* — Kenneth Crimaldi

(57) ABSTRACT

A process for producing a catalyst for the (amm)oxidation of alkanes comprises calcination of a crystalline mixed metal oxide catalyst partially or wholly in the presence of steam.

7 Claims, 1 Drawing Sheet

(51) Int. Cl.
*B01J 37/00* (2006.01)
*B01J 37/03* (2006.01)
*B01J 37/10* (2006.01)

(56) References Cited

U.S. PATENT DOCUMENTS

| | | | |
|---|---|---|---|
| 6,063,728 | A | 5/2000 | Hinago et al. |
| 6,180,825 | B1 | 1/2001 | Lin et al. |
| 6,407,280 | B1 | 6/2002 | Chaturvedi et al. |
| 6,504,053 | B1 | 1/2003 | Chaturvedi et al. |
| 6,514,901 | B1 | 2/2003 | Lin et al. |
| 6,646,158 | B1 * | 11/2003 | Karim et al. ............... 562/512.2 |
| 6,700,015 | B2 | 3/2004 | Chaturvedi et al. |
| 6,790,988 | B2 | 9/2004 | Chaturvedi et al. |
| 6,825,380 | B2 | 11/2004 | Chaturvedi et al. |
| 7,091,377 | B2 | 8/2006 | Borgmeier et al. |
| 7,304,014 | B2 | 12/2007 | Cavalcanti et al. |
| 7,875,571 | B2 | 1/2011 | Bogan, Jr. et al. |
| 2002/0123647 | A1 | 9/2002 | Bogan, Jr. et al. |
| 2007/0179042 | A1 | 8/2007 | Pessoa Cavalcanti et al. |
| 2008/0064590 | A1 * | 3/2008 | Bogan .................. B01J 23/002 502/204 |

OTHER PUBLICATIONS

X-ray Diffraction., The University of Manchester School of Materials., http://www.materials.manchester.ac.uk/our-research/facilities/x-ray-diffraction/.

X-Ray Facility Instruments. Materials Research Laboratory at UCSB: An NSF MRSEC. www.mrl.uscb.edu/centralfacilities/x-ray/instruments.

X-ray Diffraction Tubes: Seifert Analytical X-ray. GE Measurement and Control Solutions. www.ge-mcs.com. 2011.

Holmberg, et al., "A study of propane ammoxidation on Mo—V—Nb—Te-oxide catalysts diluted with Al2O3, SiO2, and TiO2", Journal of Catalysis, 243, 2006, p. 350-359.

Florea, et al., "High surface area Mo—V—Te—Nb—O catalysts: Preparation, characterization and catalytic behaviour in ammoxidation of propane", Catalysis Today, 112, 2006, p. 139-142.

Ueda, et al, "Crystalline Mo—V—O based complex oxides as selective oxidation catalysts of propane", Catalysis Today, 99, 2005, p. 43-49.

Wagner, et al., "Surface texturing of Mo—V—Te—Nb—Ox selective oxidation catalysts", Topics in Catalysis, vol. 38, Nos. 1-3, Jul. 2006, p. 51-58.

Feng, et al., "The study on the source of Te and the dispersion of TeO2 in fabricating Mo—V—Te and Mo—V—Te—Nb mixed metal oxide catalysts for propane partial oxidation", Journal of Molecular Catalysis A: Chemical, 267, 2007, p. 245-254.

* cited by examiner

STEAM RE-CALCINATION OF MIXED METAL OXIDE CATALYSTS

CROSS-REFERENCE TO RELATED APPLICATIONS

This application claims priority from provisional application Ser. No. 61/467,418, filed Mar. 25, 2011, which is incorporated herein by reference in its entirety.

BACKGROUND OF THE INVENTION

The present invention relates to mixed metal oxide (amm) oxidation catalysts.

Mixed metal oxide (MMO) catalysts are well known for (amm)oxidation of alkanes and alkenes to unsaturated carboxylic acids or nitriles. For example, U.S. Pat. No. 6,407,280 discloses MMO catalysts containing Mo or W; V or Ce; Te, Sb or Se; as well as other metals, e.g., Nb, and promoted by at least one of Ni, Pd, Cu, Ag and Au.

U.S. Pat. No. 7,875,571 discloses a method for preparing MMO catalysts by contacting an MMO with water alone at elevated temperature or water comprising a metal oxide precursor to form a modified MMO, followed by calcining the modified MMO.

U.S. Pat. No. 7,304,014 teaches preparing MMO catalysts by, after calcination, doing one or more chemical and/or physical treatments such as extraction with oxalic acid in methanol, extraction with an alcohol followed by densification by extra pressing, cryo-grinding followed by extraction with oxalic acid in methanol, and others.

Prior art processes for preparing selective MMO catalysts are complicated and can involve a large number of steps. Each additional step incurs additional costs, and can lead to catalysts that give relatively more variation in selectivity during use. It would be desirable to have a relatively simple method of preparing selective MMO catalysts.

SUMMARY OF THE INVENTION

The present disclosure provides such a process, comprising the steps of:

(a) providing a mixed metal oxide first catalyst having the empirical formula:

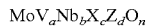
$$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, a=0.1 to 1.0, b=0.01 to 1.0, c=0.01 to 1.0, d=0 to 1.0, and n is determined by the oxidation states of the other elements; and (b) calcining the first catalyst partly or wholly in an atmosphere that comprises water vapor to form a mixed metal oxide final catalyst.

In another aspect, the disclosure provides a process for the preparation of a catalyst for the (amm)oxidation of alkanes, comprising the steps of:

(a) providing a precursor for a mixed metal oxide first catalyst, the precursor having the empirical formula:

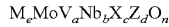
$$M_eMoV_aNb_bX_cZ_dO_n$$

wherein $M_e$ is at least one chemical modifying agent selected from the group consisting of a reducing agent, an oxidizing agent, and an alcohol, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, a=0.1 to 1.0, b=0.01 to 1.0, c=0.01 to 1.0, d=0 to 1.0, n is determined by the oxidation states of the other elements, and e is 0 or a positive number; and (b) calcining said precursor to form said mixed metal oxide first catalyst; and (c) after said calcining, re-calcining the first catalyst partly or wholly in an atmosphere that comprises water vapor to form a mixed metal oxide final catalyst.

Surprisingly, the process of the present disclosure is a simple process to improve the yield to an (amm)oxidation catalyst, i.e. steam re-calcination surprisingly improves the yield of the starting, or first, catalyst that is subjected to the process.

In one embodiment, the process of the present disclosure uses fewer steps to prepare a catalyst that provides similar, or improved, yield compared to catalysts prepared by more complex prior art methods. In addition, it minimizes the handling, e.g. transferring of the catalyst intermediate from one step to another step, of the catalyst as the precursor calcination and steam re-calcination can be conducted sequentially without removing the catalyst from the calcining furnace between the two calcination steps.

DETAILED DESCRIPTION OF THE INVENTION

Figure 1:
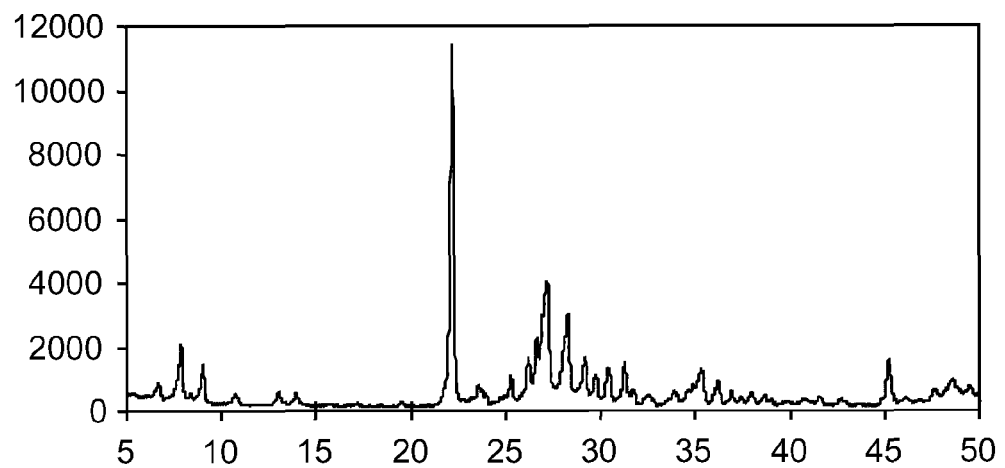
FIG. 1 is an X-ray diffraction pattern of a first catalyst prepared in Comparative Experiment 2.

In one embodiment, the process disclosed herein involves calcining a catalyst in the presence of water vapor. In one embodiment, the catalyst preparation process comprises preparing a first mixed metal oxide catalyst by calcining a precursor to produce a first catalyst, followed by calcining the first catalyst in the presence of water vapor to produce a final catalyst.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges and/or numerical values, including such recitations in the claims, can be read to include the term "about." In such instances the term "about" refers to numerical ranges and/or numerical values that are substantially the same as those recited herein.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "(meth)acrylic" refers to acrylic or methacrylic.

The catalyst that is subjected to calcination in the presence of water vapor is referred to herein as the "first catalyst."

For the process of this invention, the first catalyst can be any MMO catalyst capable of (amm)oxidizing alkanes to unsaturated carboxylic acids or nitriles. In one embodiment, the first catalyst has the empirical formula:

$$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, a=0.1 to 1.0, b=0.01 to 1.0, c=0.01 to 1.0, d=0 to 1.0, and n is determined by the oxidation states of the other elements. In one embodiment, the first catalyst is a promoted MMO in which Z is present, preferably with a value of d of from 0.001 to 0.1. Examples of promoted MMO catalysts are described, e.g., in U.S. Pat. Nos. 7,304,014, 6,825,380; 6,790,988; 6,700,015; 6,504,053 and 6,407,280. In another embodiment, Z is absent (d=0).

Preferably, when a=0.1 to 0.5, b=0.1 to 0.5, c=0.05 to 0.5, and d=0.005 to 0.5. More preferably, when a=0.2 to 0.4, b=0.15 to 0.45, c=0.05 to 0.45, and d=0.005 to 0.1. However, in an alternative embodiment, when a=0.2 to 0.3, b=0.1 to 0.3, c=0.15 to 0.3 and d=0.005 to 0.02. The value of n, i.e. the amount of oxygen present, is dependent on the oxidation state of the other elements in the catalyst. However, n is advantageously in the range of from 3.5 to 4.7. Preferably, X is Te. Preferably, Z is Pd.

The X-ray diffraction pattern of a suitable first catalyst is shown in FIG. 1. The relative peak intensities may vary slightly due to small variations in catalyst composition or calcination conditions, however, it is preferred for optimal catalytic performance in selective propane oxidation to acrylic acid that the orthorhombic phase should be the major crystal phase with main peaks with 2θ at 6.7°, 7.8°, 22.1°, and 27.2°.

The MMO first catalyst can be formed from a precursor according to methods well known to those skilled in the art. For example, the precursor can be prepared using an aqueous slurry or solution comprising solutions containing the MMO component metals. Water can be removed by any suitable method known in the art to form a catalyst precursor. Such methods include, without limitation, vacuum drying, freeze drying, spray drying, rotary evaporation and air drying. Conditions for drying MMO catalyst precursors are known and may be found in the patents cited hereinabove.

The precursor for the mixed metal oxide first catalyst advantageously can have the empirical formula:

$$M_eMoV_aNb_bX_cZ_dO_n$$

wherein $M_e$ is at least one chemical modifying agent selected from the group consisting of a reducing agent, an oxidizing agent, and an alcohol, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, a=0.1 to 1.0, b=0.01 to 1.0, c=0.01 to 1.0, d=0 to 1.0, n is determined by the oxidation states of the other elements, and e is 0 or a positive number.

Once obtained, the catalyst precursor can be calcined to form the MMO first catalyst. Calcination of the catalyst precursor is referred to hereinafter as the "precursor calcination." The precursor calcination may be conducted partially in an oxygen-containing atmosphere or in the substantial absence of oxygen, e.g., in an inert atmosphere or in vacuo. The inert atmosphere may be any material that is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a gas hourly space velocity of from 1 to 500 hr.$^{-1}$.

The precursor calcination is advantageously performed at a temperature of from 350° C. to 850° C. Preferably, the precursor calcination is performed at least at 400° C., more preferably at least at 500° C. Preferably, the maximum precursor calcination temperature is 750° C., more preferably 700° C. The precursor calcination is performed for an amount of time suitable to form the aforementioned first catalyst. Advantageously, the precursor calcination is performed for from 0.1 to 72 hours, preferably from 0.5 to 25 hours, more preferably for from 0.5 to 6 hours, to obtain the desired first catalyst.

In a preferred mode of operation, the catalyst precursor is calcined in two stages, i.e. the precursor calcination has two stages. In the first stage of the precursor calcination, the catalyst precursor advantageously is calcined in an inert or oxidizing environment (e.g. air) at a temperature of from 200° C. to 330° C., preferably from 275° C. to 325° C. for from 15 minutes to 40 hours, preferably for from 0.5 to 6 hours. In the second stage of the precursor calcination, the material from the first stage advantageously is calcined in a non-oxidizing environment (e.g., an inert atmosphere) at a temperature of from 500° C. to 750° C., preferably for from 550° C. to 650° C., for 0.2 to 25 hours, preferably for from 1 to 3 hours.

In a particularly preferred mode of operation, the catalyst precursor in the first stage of the precursor calcination is placed in the desired oxidizing atmosphere at room temperature and is then heated to the first stage calcination temperature and held there for the desired first stage calcination time. The atmosphere is then replaced with the desired non-oxidizing atmosphere for the second stage of the precursor calcination, and the temperature is then raised to the desired second stage calcination temperature and held there for the desired second stage calcination time.

Once obtained, the first catalyst can be calcined to form the final catalyst. The calcination of the first catalyst is conducted in the presence of water vapor, such as steam. This calcination is referred to hereinafter as the steam re-calcination. Advantageously, the steam re-calcination produces a catalyst that may be employed to produce an (amm)oxidation process product, such as acrylic acid, in a higher yield, measured at 85% oxygen conversion, than the first catalyst from which it is prepared.

In one embodiment, the average amount of water vapor present in the steam re-calcination is from about 0.01 to about 100, preferably from 0.5 to 10, more preferably from 1 to about 3.5, volume percent, based on the total volume of gas in the calcining vessel. The steam re-calcination may be conducted partially in an oxygen-containing atmosphere or in the substantial absence of oxygen, e.g., in an inert atmosphere or in vacuo. The inert atmosphere may be any material that is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr.$^{-1}$.

The steam re-calcination advantageously is performed at a temperature of from 100° C. to 650° C. Preferably, the steam re-calcination is performed at a temperature of at least 300° C. Preferably, the maximum steam re-calcination temperature is 650° C., more preferably 550° C. The steam re-calcination suitably is performed for an amount of time suitable to form the final catalyst. Advantageously, the steam re-calcination is performed for from 0.1 to 72 hours, preferably from 0.5 to 25 hours, more preferably for from 1 to 10 hours, to obtain the desired calcined final modified mixed metal oxide.

Water vapor can be introduced at any time in the steam re-calcination. When two stages are employed in the steam re-calcination, water vapor can be introduced in either the first stage, second stage, or both stages. The water vapor can be present through a whole stage of the calcination, or only part of a stage. In a particularly preferred mode of the operation, the water vapor is introduced at least in the first stage of the steam re-calcination.

Water vapor can be introduced alone or together with a carrier gas. In one mode of operation, the water vapor is introduced by passing a carrier gas through a water saturator that is maintained at room temperature. In another mode of operation, the water can be injected in liquid form and then immediately vaporized into vapor prior to contacting the catalyst. Other modes of operation are also possible, such as generating water vapor and introducing it directly into the calcination vessel.

The water vapor can flow through the catalyst particles, or contact the catalyst particles in static mode, as long as substantial contact of water vapor with the catalyst particles occurs.

The purity of the water vapor is not particularly critical, although it is preferred that the purity does not have a substantial negative impact on catalyst performance. In one preferred mode of operation, deionized water is employed.

In a preferred mode of operation, the first catalyst advantageously is calcined in two stages in the steam re-calcination step. In the first stage, the first catalyst advantageously is calcined in an inert or oxidizing environment (e.g. air) at a temperature of from 100° C. to 400° C., preferably from 275° C. to 325° C. for from 15 minutes to 40 hours, preferably for from 0.5 to 6 hours. In the second stage, the material from the first stage advantageously is calcined in a non-oxidizing environment (e.g., an inert atmosphere) at a temperature of from 400° C. to 650° C., preferably for from 450° C. to 550° C., for 0.5 to 25 hours, preferably for from 1 to 3 hours.

In a particularly preferred mode of operation, the first catalyst in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of calcination vessel and heating mechanism, e.g., a furnace, may be utilized during calcination, it is preferred to conduct calcination under a flow of the designated gaseous atmosphere. Therefore, it is advantageous to conduct calcination in a bed with continuous flow of the desired gas(es) through the bed of solid catalyst or catalyst precursor particles.

The first and/or final metal oxide catalyst may be ground at any point in the process, following or prior to any of the treatment steps. In a preferred embodiment, only the final catalyst is ground. Preferably, the surface area after grinding is from 5-30 m$^2$/g, and more preferably is from 10-18 m$^2$/g. Examples of suitable types of grinding apparatus include, e.g., a freezer/mill, ball mill, mortar and pestle, and jet mill.

The final catalyst can be used as an (amm)oxidation catalyst. For example, it can be employed to oxidize propane to acrylic acid. Similarly, methacrylic acid can be produced by isobutane oxidation. In addition to (meth)acrylic acid, (meth)acrylonitrile can be produced by oxidizing propane or isobutane in the presence of air and ammonia. Although the catalyst shows big advantages when used in alkane (amm) oxidation, it can be used in (amm)oxidation of olefins or a mixture of olefins and alkanes.

SPECIFIC EMBODIMENTS OF THE INVENTION

The following examples are given to illustrate the invention and should not be construed as limiting its scope.

EXAMPLES

Comparative Experiment 1—Synthesis of MMO Precursor

A mixed oxide first catalyst of nominal composition $Mo_{1.0}V_{0.285}Te_{0.21}Nb_{0.164}Pd_{0.01}O_n$ is produced from a MMO precursor prepared in the following manner:

(1) An aqueous solution containing Mo(VI), V(V), and Te(IV) salts is formed by dissolving ammonium heptamolybdate tetrahydrate (35.7 g, from Fisher Scientific), ammonium metavanadate (6.7 g, from Sigma Aldrich) and telluric acid (9.7 g, from Sigma Aldrich) sequentially in 200 ml of deionized (D.I.) water that is pre-heated to 70° C. The mixed salt solution is stirred for 20 minutes at 70° C. to ensure that a clear solution is formed. Then, 5 ml of concentrated nitric acid (70 wt. % in water, from Sigma Aldrich) is added to the solution under stirring.

(2) Separately, an aqueous solution containing ammonium niobium oxalate (15.7 g, from H.C. Starck, Goslar, Germany) and oxalic acid dihydrate (3.9 g, from Sigma Aldrich) in 180 cc D.I. water is prepared at room temperature.

(3) The Mo/V/Te solution is held under stirring with heating. Then, the heating is stopped and the Nb-containing solution is added to the Mo/V/Te. Gelation occurs immediately after the two solutions are mixed. The mixture is stirred for 5 minutes and becomes a slurry before being transferred to a round-bottom rotary flask.

(4) The water in the slurry is removed via a rotary evaporator at 50° C. under a vacuum of 10-50 mmHg (1.33-6.67 kPa). The solid material is further dried in a vacuum oven overnight at room temperature. This dried material is designed as the "MMO precursor."

Comparative Experiment 2—Calcination of MMO Precursor

The MMO precursor (15-20 grams) prepared in Comparative Experiment 1 is placed in the middle of a quartz tube with quartz wool stuffed into the tube at both ends of the solid bed of precursor. The precursor is calcined by heating the tube furnace from room temperature to 275° C. at 10° C./min in flowing air (80-100 standard cubic centimeters per minute, hereinafter SCCM) and holding the temperature at 275° C. for one hour. The flowing gas is then switched to inert gas such as argon or nitrogen (80-100 SCCM). The furnace temperature is raised to 615° C. from 275° C. at 2° C./min and held at 615° C. in an inert gas atmosphere for two hours. This results in a first catalyst of nominal composition $Mo_{1.0}V_{0.285}Te_{0.21}Nb_{0.164}Pd_{0.01}O_n$.

The MMO solid first catalyst has an X-ray diffraction pattern as shown in FIG. 1.

Comparative Experiment 3—Grinding of MMO First Catalyst

The MMO first catalyst of Comparative Experiment 2 is broken into smaller pieces and passed through 10 mesh sieves. The sieved particles are ground with a 6850 Freezer/Mill (from SPEX Certiprep, located at Metuchen, N.J., USA). Grinding time is adjusted to get a final ground material having a surface area in the range of 12-14 m$^2$/g. This results in a ground first catalyst of nominal composition $Mo_{1.0}V_{0.285}Te_{0.21}Nb_{0.164}Pd_{0.01}O_n$.

Example 1—Preparation of MMO Final Catalyst with Steam Introduction at 100° C.

A MMO first catalyst with the composition $Mo_{1.0}V_{0.285}Te_{0.21}Nb_{0.164}Pd_{0.01}O_n$ is prepared by following the procedure of Comparative Experiments 1 and 2. The first catalyst is re-calcined in the presence of steam in the same tube furnace. This post calcination is hereinafter designated a "steam re-calcination" step. The carrier gas air flows through a glass water saturator held at room temperature, and then passes through the catalyst bed. The water concentration in the flowing air is 3.0 volume % based on the equilibrium water partial pressure at room temperature (22-25° C.). In this example, the temperature of the furnace is increased from ambient temperature to 100° C. with a ramp rate of 5° C./min, and then is held for three hours at 100° C. Then, the flowing air bypasses the water saturator and continues flowing through the catalyst bed, i.e. water vapor is no longer introduced, while the bed temperature is raised at 5° C./min to 300° C. and is held there for three hours. After calcination at 300° C., the flowing gas is switched to argon and the bed temperature is raised at 2° C./min to 500° C. and is held there for two hours. The re-calcined material is ground to fine powder following the procedure of Comparative Experiment 3.

Example 2—Preparation of MMO Final Catalyst with Steam Introduction at 200° C.

The procedure of Example 1 is repeated except that the steam introduction temperature is 200° C.

Example 3—Preparation of MMO Final Catalyst with Steam Introduction at 300° C.

Figure 2:
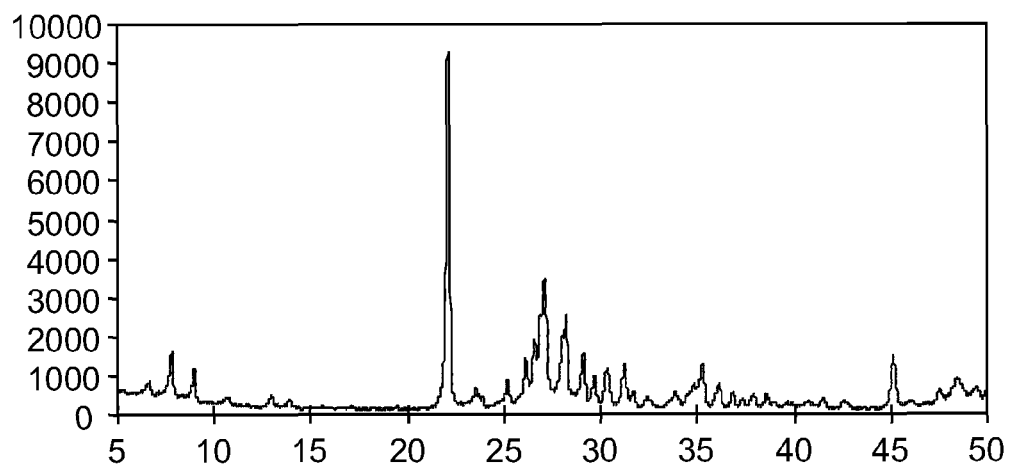
FIG. 2 is an X-ray diffraction pattern of a final catalyst prepared in Example 3.

The procedure of Example 1 is repeated except that the steam introduction temperature is 300° C. The MMO final catalyst after the re-calcination in steam and air/argon has an X-ray diffraction pattern as shown in FIG. 2.

Example 4—Preparation of MMO Final Catalyst with Re-Calcination Under Steam at 300° C. and no Air Re-Calcination at 300° C.

The procedure of Example 1 is repeated except that (1) the steam is introduced while the catalyst is heated to 300° C. and is held at 300° C. for 3 hours, and (2) the air re-calcination at 300° C. following steam re-calcination is skipped.

Example 5—Preparation of MMO Final Catalyst with Re-Calcination Under Steam at 300° C. and 500° C.

The procedure of Example 1 is repeated except that: (1) the steam is introduced while the catalyst is heated to 300° C. and is held at 300° C. for 3 hours, (2) the air re-calcination at 300° C. following steam re-calcination is skipped, and (3) steam is introduced continuously during the re-calcination to and at 500° C. in argon.

Comparative Experiment 4—Preparation of MMO Comparative Catalyst with Re-Calcination without Steam The procedure of Example 1 is repeated except that the steam introduction to and at 100° C. is skipped. The catalyst is re-calcined in flowing air first at 300° C. for 3 hours, and then in flowing argon at 500° C. for 2 hours.

Comparative Experiment 5—Preparation of MMO Comparative Catalyst with Steam Introduction During MMO Precursor Calcination at 275° C.

A MMO catalyst with the composition $Mo_{1.0}V_{0.285}Te_{0.21}Nb_{0.164}Pd_{0.01}O_n$ is prepared following the procedure of Comparative Experiment 3 except that steam is introduced during precursor calcination to and at 275° C. The steam is introduced by passing the air through a water saturator held at room temperature prior to sending the air through the catalyst bed.

Comparative Experiment 6—Preparation of MMO Comparative Catalyst with Steam Introduction During the Entire MMO Precursor Calcination Step A MMO catalyst with the composition $Mo_{1.0}V_{0.285}Te_{0.21}Nb_{0.164}Pd_{0.01}O_n$ is prepared following the procedure of Comparative Experiment 3 except that steam is introduced during the entire precursor calcination process. The steam is introduced by passing the carrier gas through a water saturator held at room temperature prior to sending the carrier gas through the catalyst bed.

Comparative Experiment 7—Preparation of MMO Comparative Catalyst with Subsequent Water Wetting at Room Temperature and Re-Calcination/Grinding 20 grams of the first catalyst of Comparative Experiment 2 is stirred in D.I. water (50 g) for twenty minutes, and dried via a rotary evaporator at 50° C. under a vacuum of 10-50 mmHg (1.33-6.67 kPa). The dried material is then calcined in flowing air at 300° C. for 3 hours, and then calcined in flowing argon at 500° C. for 2 hours. This re-calcined material is then ground following the procedure of Comparative Experiment 3.

Comparative Experiment 8—Preparation of MMO Comparative Catalyst with Contacting Water Under Reflux Condition and Re-Calcination/Grinding Steps 20 grams of this the calcined first catalyst of Comparative Experiment 2 is heated in D.I. water (50 g) under reflux for 5 hours. The resulting material is collected by vacuum filtration and dried in a vacuum oven at room temperature overnight. The dried material is first calcined in flowing air at 300° C. for 3 hours, and then calcined in flowing argon at 500° C. for 2 hours. This re-calcined material is ground following the procedure of Comparative Experiment 3.

Comparative Experiment 9—Preparation of MMO Comparative Catalyst with Extraction Step 10 grams of the first catalyst of Comparative Experiment 3 is added to 100 grams of an aqueous solution containing 2 wt. % of oxalic acid. The mixture is stirred under reflux for 5 hours. The material is collected by vacuum filtration and dried in a vacuum oven at room temperature overnight.

Comparative Experiment 10—Preparation of MMO Comparative Catalyst with Multiple Synthesis Steps Including Impregnation and Extraction A MMO catalyst with the composition $Mo_{1.0}V_{0.285}Te_{0.21}Nb_{0.164}Pd_{0.01}O_n$ is synthesized following the sequence of multiple steps listed below:

(a) a MMO precursor is synthesized following the procedure of Comparative Experiment 1;

(b) the MMO precursor is calcined as in Comparative Experiment 2;

(c) the calcined MMO is impregnated with tellurium and niobium. 60 grams of the calcined MMO catalyst of step (b) is added to a solution containing telluric acid (0.54 g, from Sigma Aldrich), ammonium niobium oxalate (0.75 g, from H.C. Starck located at Goslar, Germany), and 100 grams of D.I. water. The resulting mixture is stirred for 20 minutes at room temperature and dried via a rotary evaporator at 50° C. under a vacuum of 10-50 mmHg (1.33-6.67 kPa). This step is designated as the "impregnation" step.

(d) 10 grams of the dried material impregnated with tellurium and niobium is re-calcined first in flowing air at 300° C. for 3 hours, and then in flowing argon at 500° C. for 2 hours;

(e) The re-calcined material is ground following procedure in Comparative Experiment 3;

(f) 10 grams of the ground powder is added to 100 grams of an aqueous solution containing 2 wt. % of oxalic acid under stirring. The mixture is heated to reflux and is maintained at reflux for 3 hours;

(g) The resulting solid material is collected by vacuum filtration and is dried in a vacuum oven at room temperature overnight.

Evaluation of MMO Catalysts for Propane Oxidation to Acrylic Acid

The catalysts obtained from the above examples and comparative experiments are each pressed and sieved to 14-20 mesh granules. 4 grams of granules of each catalyst are packed into a stainless steel plug flow tubular reactor (inside diameter: 1.1 cm) with silicon carbide inert particles loaded above and below the catalyst charge. The reactor tube is installed in an electrically heated clamshell furnace. The catalyst bed is preheated to 180° C. in a 50 SCCM $N_2$ flow, and then the gas feed is switched to a gas mixture feed containing 7 vol. % propane, 70 vol. % air, and 23 vol. % steam. Steam is provided by injecting D.I. water via a syringe pump into a pre-heating zone set at 180° C. The flow rate of the feed is controlled at 80 SCCM with a residence time of 3 seconds. The catalyst bed temperature is adjusted to obtain the desired conversion of oxygen.

The effluent of the reactor is condensed by a cold trap submerged in an ice/water bath to collect condensable products. Reaction product vapor exiting the cold trap is analyzed by a gas chromatograph equipped with a thermal conductivity detector and molecular/silical gel columns. The condensed liquid products are analyzed by a gas chromatograph fitted with a flame ionization detector and an Alltech ECONO-CAP EC-1000 capillary column (30 m×0.53 mm ID×1.2 µm).

The conversion of $O_2$ is calculated by difference as follows, where $n_i$ denotes the molar flow rate of species i:

$$O_2 \text{ conversion } (\%) = 100 \times \left(1 - \frac{n_{O2}^{out}}{n_{O2}^{in}}\right)$$

The yield of acrylic acid (AA) is calculated as follows:

$$AA \text{ yield } (\%) = 100 \times \frac{(n_{AA}^{out} - n_{AA}^{in})}{(n_{propane}^{in} - n_{propane}^{out})}$$

Acrylic acid yields of the different catalysts are compared at a constant $O_2$ conversion of 85%. In the manufacture of acrylic acid from propane, it is desirable to maximize reactor productivity, to maximize selectivity to product, to avoid the creation of a flammable mixture of gases, and to maximize catalyst lifetime. To maximize productivity, concentrations of propane and oxygen in the reactor feed are increased. To maximize product yield, the concentration of water (steam) in the feed is increased. To avoid the creation of a flammable mixture of gases, the ratio of fuel to oxygen in the feed is controlled. To maximize catalyst lifetime, a minimal amount of oxygen is maintained in the reactor effluent. The net effect of the feed constraints is to require a feed mixture in which the ratio of propane to oxygen is nearly stoichiometric. That is, for the conversion of propane to acrylic acid, the ratio of propane to oxygen is about 1:2.1. Since the formation of waste products (carbon oxides, acetic acid) requires a greater amount of oxygen, and their formation is unavoidable, oxygen becomes the limiting reagent in the reaction. For this reason, it is preferred to measure catalyst performance as yield of (or selectivity to) acrylic acid as a function of oxygen conversion, rather than propane conversion.

All the catalyst samples are tested under the same conditions, such as feed composition and residence time, as described above. However, the reaction temperature is varied among different samples due to activity differences in order to achieve 85% $O_2$ conversion. The yields of acrylic acid at 85% $O_2$ conversion over different samples are listed in Table 1.

TABLE 1

Yield of acrylic acid over different MMO catalyst samples synthesized under different conditions/steps

| | Steps Involved for MMO Catalyst Synthesis Starting from MMO Precursor | | | | | | | |
|---|---|---|---|---|---|---|---|---|
| | Precursor | Impreg- | Mixing | Re-calcination (° C.) | | Extraction & | | AA |
| Example | Calcination (° C.) | nation & Drying | w/water & Drying** | with steam | without steam | Filtration & Drying | Grinding | Yield (%) |
| CE 3* | X | | | | | | X | 54.0 |
| 1 | X | | | X (100) | X (300/500) | | X | 56.9 |
| 2 | X | | | X (200) | X (300/500) | | X | 57.1 |
| 3 | X | | | X (300) | X (300/500) | | X | 57.6 |
| 4 | X | | | X (300) | X (500) | | X | 57.5 |
| 5 | X | | | X (300/500) | | | X | 56.3 |
| CE 4* | X | | | | X (300/500) | | X | 54.5 |
| CE 5* | X (w/steam at 275) | | | | | | X | 54.6 |
| CE 6* | X (w/steam at 275/615) | | | | | | X | 54.0 |
| CE 7* | X | | X (mixing at r.t.) | | X (300/500) | | X | 56.0 |
| CE 8* | X | | X (refluxing in water) | | X (300/500) | | X | 53.0 |
| CE 9* | X | | | | | X | X | 56.0 |
| CE 10* | X | X | | | X | X | X | 59.0 |

*CE = Comparative Experiment - not an embodiment of the invention.
**the catalyst particles are recovered by filtration after refluxing in water.

These results clearly demonstrate the benefits of steam re-calcination of the first MMO catalyst to prepare the final catalyst. As shown in Table 1, MMO final catalysts prepared by simple steam re-calcination of a MMO first catalyst show an AA yield of around 57%, which is about 3-4% higher than the yield achieved using the first MMO catalyst of C.E. 3, which is prepared without further steam re-calcination.

The re-calcined catalysts also unexpectedly show improved AA yield compared to the comparative catalysts prepared by more complex methods of C.E.s 4-9.

While the MMO catalyst prepared via multiple steps as shown in Comparative Experiment 10 gives an AA yield of 59%, its preparation involves at least eight steps (both filtration and drying are counted as single step) with frequent transferring of the catalyst intermediate between different steps. These multiple synthesis steps not only increase the catalyst cost significantly, but increase the risk of variation of the final catalyst performance.

What is claimed is:

1. A process, comprising the steps of:
   (a) providing a mixed metal oxide first catalyst having the empirical formula:

$MoV_aNb_bX_cZ_dO_n$ and an X-ray diffraction pattern showing the orthorhombic phase as the major crystal phase with main peaks with 2θ at 6.7°, 7.8°, 22.1°, and 27.2°, wherein X is Te, Z is Pd, a=0.2 to 0.3, b=0.1 to 0.3, c=0.15 to 0.3, d=0.005 to 0.02, and n is determined by the oxidation states of the other elements; wherein a catalyst precursor is dried and then calcined at a temperature from 550 to 650° C. in an inert atmosphere consisting of nitrogen, argon, xenon, helium or mixtures thereof to produce the first catalyst; and
   (b) calcining the first catalyst at ambient atmospheric pressure at a temperature from 100 to 550° C. partly or wholly in an atmosphere that comprises water vapor to form a mixed metal oxide final catalyst.

2. The process of claim 1 further comprising: (c) grinding the mixed metal oxide final catalyst.

3. The process of claim 1 wherein the water vapor comprises from 0.01 to 100 volume percent, based on the total volume of gas in the atmosphere.

4. The process of claim 1 wherein the water vapor comprises from 0.5 to 10 volume percent, based on the total volume of gas in the atmosphere.

5. The process of claim 1 wherein the water vapor comprises from 1 to 3.5 volume percent, based on the total volume of gas in the atmosphere.

6. The process of claim 1 wherein calcining the catalyst precursor is done in 2 stages, wherein, in the first stage, the catalyst precursor is calcined in an inert or oxidizing environment at a temperature of from 200 to 330° C., for from 15 minutes to 40 hours, and in a second stage the material from the first stage is calcined in an inert atmosphere at a temperature of from 550 to 650° C. for 0.1 to 25 hours.

7. The process of claim 1 wherein the first catalyst has the empirical formula: $MoV_aNb_bX_cZ_dO_n$ wherein a is 0.285, b is 0.164, c is 0.21, and d is 0.01.

* * * * *